(12) United States Patent
Bhardwaj et al.

(10) Patent No.: US 7,022,853 B2
(45) Date of Patent: Apr. 4, 2006

(54) SINGLE POT PROCESS FOR PREPARING METAL NICOTINATES FROM BETA-PICOLINE

(75) Inventors: Nikhilesh Chandra Bhardwaj, Noida (IN); Pradeep Kumar Verma, Noida (IN); Agarwal Ashutosh, Noida (IN)

(73) Assignee: Jubilant Organosys Ltd., Noida (IN)

( * ) Notice: Subject to any disclaimer, the term of this patent is extended or adjusted under 35 U.S.C. 154(b) by 454 days.

(21) Appl. No.: 10/282,210

(22) Filed: Oct. 29, 2002

(65) Prior Publication Data

US 2003/0114676 A1 Jun. 19, 2003

Related U.S. Application Data

(63) Continuation-in-part of application No. 09/983,897, filed on Oct. 26, 2001, now Pat. No. 6,486,318.

(51) Int. Cl.
*C07F 3/06* (2006.01)
*C07F 11/00* (2006.01)

(52) U.S. Cl. .......................................... 546/5; 546/320
(58) Field of Classification Search ................ 546/5, 546/320
See application file for complete search history.

(56) References Cited

U.S. PATENT DOCUMENTS

| | | |
|---|---|---|
| 2,437,938 A | 3/1948 | Cislak et al. |
| 2,513,099 A | 6/1950 | Mueller |
| 2,522,163 A | 9/1950 | Cislak et al. |
| 4,020,158 A | 4/1977 | Ashmead et al. |
| 4,021,569 A | 5/1977 | Abdel-Monem |
| 4,167,564 A | 9/1979 | Jensen |
| 4,315,927 A | 2/1982 | Evans |
| 4,923,855 A | 5/1990 | Jensen |
| RE33,988 E | 7/1992 | Evans |
| 5,194,615 A | 3/1993 | Jensen |
| 5,582,817 A | 12/1996 | Otsu et al. |
| 5,677,461 A | 10/1997 | Lee |
| 5,696,169 A | 12/1997 | Otsu et al. |
| 6,139,881 A | 10/2000 | Thompson |
| 6,203,819 B1 | 3/2001 | Fine |
| 6,379,693 B1 | 4/2002 | Mao et al. |
| 6,486,318 B1 | 11/2002 | Kumar et al. |

FOREIGN PATENT DOCUMENTS

WO    WO 02/36202    5/2002

OTHER PUBLICATIONS

National Academy of Sciences, 1980 p. 160.
J. Org. Chem. 14, 14 (1949).
J. Chem. Soc. 934 (1946).

*Primary Examiner*—Bernard Dentz
(74) *Attorney, Agent, or Firm*—Lowe Hauptman Gilman & Berner LLP

(57) ABSTRACT

The present invention relates to a single-pot process for the preparation of metal nicotinates, useful as a dietary supplement, from beta picoline as a source of the starting material, said process comprising the steps hydrosulfonation of beta picoline with sulfuric acid, heating the reaction mixture thus obtained to a temperature of about 150°–210° C. followed by oxidation with a suitable oxidizing agent to obtain nicotinic acid sulfate, reacting the nicotinic acid sulfate with a water soluble zinc and/or chromium salt to produce a solid metal nicotinate and separating it to thereby recover the corresponding metal nicotinates of high purity.

23 Claims, No Drawings

SINGLE POT PROCESS FOR PREPARING METAL NICOTINATES FROM BETA-PICOLINE

This application is a Continuation-in-Part of U.S. patent application Ser. No. 09/983,897, filed Oct. 26, 2001, now U.S. Pat. No. 6,486,318, the entire contents of which are incorporated herein by reference.

FIELD OF INVENTION

The present invention relates to a single-pot process for the preparation of metal nicotinates that are useful as a dietary supplement. Beta picoline is the source of starting material for this process.

BACKGROUND OF THE INVENTION

The incorporated parent patent application discloses a single pot process for the preparation of metal picolinates.

In 1996, according to WHO and the International Diabetes Federation, there were 132 million diabetic patients worldwide. This number is expected to increase to 240 millions by 2010. Diabetes is a serious disease that we need to cure.

Trivalent chromium in a trace amounts, is needed by for the metabolism of sugar, protein and fat in the human body. A deficiency of this trace element causes diabetes. Trivalent chromium is distributed in many tissues in human body, with liver and kidney containing the highest amount.

According to a report published in the National Academy of Sciences, in 1980, at page 160, only 0.5% of ingested inorganic chromium is assimilated into the body. Also only 1–2% of most ingested organic chromium compounds is assimilated into the body. In marked contrast to this, the synthetic coordination complex of picolinic acid with chromium is directly available for absorption without competition from other metals as reported in U.S. reissue Pat. No. Re 33988. Published U.S. Patent Application No. 2002 098247 and published PCT application WO 02/36202 disclose that chromium nicotinate composition is used to improve insulin sensitivity, reduces hyperglycemia and reduces hypercholesterolemia.

U.S. Pat. Nos. 6,379,693 and 6,203,819 reveal that chromium nicotinate can be administered as a dietary supplement to the patients for curing diabetes. According to U.S. Pat. No. 5,194,615 it can also be used as Glucose Tolerance Factor (GTF) treatment material. Chromium nicotinate is also reported to be useful as a feed supplement to cattle to improve their milk production (U.S. Pat. No. 6,139,881).

Zinc, a trace element in the human body, is known to participate in the development of sexual organs, promotion of wound healing, activating the immune system and to be a component of a metalloenzyme, which is an accelerator for dehydrogenase. Conventionally zinc oxide formulations have been topically used as medicines for treating skin diseases such as dermatitis, sunburn, neurodermatitis and eczema. These formulations have local astringent action and irritation, and are not usually administered internally. U.S. Pat. Nos. 5,582,817 and 5,696,169 reported that zinc nicotinate can be used in cosmetics and as a drug for ameliorating sunburn and skin diseases, preventing sunburn, relieving irradiation disorders, etc.

In the prior art of preparation of chromium nicotinate, U.S. Pat. Nos. 5,194,615 and 4,923,855 suggested the reaction of an alkali metal salt of nicotinic acid with a trivalent chromium salt. After the completion of reaction, the precipitated chromium complex is filtered and dried.

Further U.S. Pat. Nos. 5,696,169 and 5,582,817 discloses the preparation of zinc nicotinate complex by reacting nicotinic acid with zinc acetate dihydrate, and adjusting the pH to 8.5. However these patents use nicotinic acid and chromium (III) chloride hexahydrate or zinc acetate dihydrate as the starting material for the manufacturer of chromium nicotinate or zinc nicotinate, respectively.

Alkylpyridines can be oxidised by chemical agents such as $KMnO_4$ but these reagents are expensive and can lead to excessive oxidation and thereby cause ring degradation [*J. Org. Chem.* 14, 14 (1949); *J. Chem. Soc.* 934 (1946)] and generates allot of $MnO_2$ as solid waste, which has its own problems in disposal. Other methodologies include nitric acid oxidation, which has been reported as a more economical route, but it requires elevated temperature and pressure [Bengtsson, *Acta. Chem. Scand.*; 9, 832 (1955)]. These harsh conditions cause decarboxylation and thus resulting yield loss of pyridine carboxylic acid. U.S. Pat. No. 2,437,938 reports catalytic air oxidation, but doesn't appear to have general application.

U.S. Pat. No. 2,522,163 relates to preparation of pyridine carboxylic acids from sulfates of alkyl pyridine, quinoline, isoquinolines and alkyl quinolines. That invention is illustrated by an example wherein the preparation of nicotinic acid from beta picoline (3-picoline) is described.

U.S. Pat. No. 2,513,099 discloses a process for oxidising N-heterocyclic compounds containing a pyridine nucleus and an oxidizable organic group attached to the nitrogen containing aromatic nucleus by at least one carbon to carbon linkage. The process involves oxidation by reacting nitric acid with a solution containing the N-heterocyclic compound and a mixture of mercury and copper compounds dissolved in sulphuric acid. This process of oxidation may normally lead to the contamination of the nicotinic acid with undesired metals. While the prior art techniques for preparing chromium nicotinate and zinc nicotinate have been reasonably successful, the presently known and used preparation is rather complex. These techniques involve multi-steps, which makes the product expensive.

OBJECTS OF THE INVENTION

Therefore, it is an object of the present invention to produce chromium nicotinate and/or zinc nicotinate from a cheaper raw material (beta picoline) using a single pot process.

The main object of the present invention is to provide a novel single pot process for the preparation of metal nicotinates using beta picoline as a source of starting material.

Another objective of the present invention is to use metal nicotinates produced by a single pot process as a dietary supplement.

SUMMARY OF THE INVENTION

Accordingly, the present invention provides a single pot process for the preparation of metal nicotinates as a dietary supplement from beta picoline as a cheaper source of raw material. These metal nicotinates have unexpectedly high purity.

DETAILED DESCRIPTION OF THE INVENTION

The present invention relates to a single pot process for the preparation of metal nicotinates, which are useful as dietary supplement, used as a drug or in the formulation of cosmetics, ointments, etc., from beta picoline. The said process comprises the steps of:

(a) hydrosulfonation of beta picoline with sulfuric acid at a temperature of about 35–100° C. to form a reaction mixture;

(b) further heating the reaction mixture thus obtained to a temperature of about 150°–210° C.;

(c) oxidizing the reaction mixture of step (b) with an oxidizing agent at a temperature of about 50–90° C., to form an aqueous solution comprising nicotinic acid sulfate;

(d) bringing, or maintaining, the pH of the solution produced in step (c) at a pH of about 7 to 8 (a mildly basic solution);

(e) treating the basic solution of step (d) with a water soluble zinc and/or chromium salt to produce a solid metal nicotinate in said water, and (f) filtering the resulting solid metal nicotinate to remove such from said water and to thereby obtain the corresponding metal nicotinates of high purity.

In another embodiment of the present invention, the reaction of beta picoline with sulphuric acid in step a) is carried out in the temperature range of about 35° to 90° C.

In still another embodiment of the present invention, the reaction of the beta picoline with sulphuric acid in step a) is carried out in the temperature range of about 60–80° C.

In yet another embodiment of the present invention, the reaction mass is heated in step b) up to a temperature of about 150°–210° C.

In yet another embodiment of the present invention, the reaction mass is heated in step b) up to a temperature of about 190°–205° C.

In still another embodiment of the present invention, the oxidising agent used in step c) is about 40–70% concentrated nitric acid.

In still another embodiment of the present invention, proper ventilation is provided for removal of nitric oxide fumes produced during oxidation in step c).

In another embodiment of the present invention, oxidation in step c) is carried out for about 18–22 hrs, more preferably for about 20 hrs.

In another embodiment of the present invention, the reaction mixture is diluted in step d) with water before adjusting the pH.

In an embodiment of the present invention, the reaction mixture is cooled to an ambient temperature in step d) before dilution with water in step.

In an embodiment of the invention, the pH of the reaction mixture is adjusted in step d) to a pH of about 7.0 to 8.0 with an aqueous alkali solution In yet another embodiment of this invention, the aqueous alkali solution used in step d) is an aqueous ammonia solution.

In still another embodiment of the invention, the reaction mixture having a pH of about 7.0 to 8.0 is heated in step d) to about 80 to 90° C. and is thereafter treated in step e) with said metal salts.

In another embodiment of the present invention, the metal salt used in step e) for preparation of chromium nicotinate comprises at least one of chromium (III) nitrate, chromium (III) chloride, chromium (III) acetate, chromium (III) formate and chromium (III) sulphate.

In another embodiment of the present invention, chromium nicotinate having about 8–14% chromium content is obtained as the product of step f).

In yet another embodiment of the present invention, chromium nicotinate having about 12.7 to 12.9% chromium content is obtained as a product from step f).

In one more embodiment of the present invention, the metal salt used for the preparation of zinc nicotinate is at least one of zinc sulphate, zinc chloride, zinc acetate and zinc carbonate.

In another embodiment of the present invention, zinc nicotinate having about 19–22% zinc content is obtained from step f).

In another embodiment of the present invention, zinc nicotinate having about 21% zinc content is obtained from step f).

In another embodiment of the present invention, pure metal nicotinates are obtained by filtering, washing and drying the reaction product of steps a) to e).

In one more embodiment of the present invention, unreacted beta picoline is recovered from the filtrate.

In another embodiment, the present invention provides a means of utilizing a cheaper raw material and an economical single-pot preparation of a high purity metal nicotinate product. Beta picoline is used in the preparation of metal nicotinates instead of nicotinic acid, which has been used in the prior art for preparation and which is also a much costlier raw material in comparison to beta picoline.

In still another embodiment of the present invention, beta picoline is reacted in step a) with sulfuric acid at a temperature ranging of about 35–90° C. and most preferably about 60–80° C. After the addition of beta picoline, the reaction mass temperature is raised to a temperature of about 150–210° C., preferably between 190–205° C. Nitric acid, at a concentration of about 40–70%, is added. More preferably the concentration of nitric acid is about 54–60%. The oxidation leads to evolution of nitric oxide fumes, which are properly vented or scrubbed. The nitric acid is added over a period of about 18–22 hrs, and more preferably in less than about 20 hrs. The reaction mass is then cooled to an ambient temperature, diluted with water, followed by adjusting the pH to between about 7.0 to 8.0 using aqueous ammonia. The reaction mass is again heated to about 50–100° C., preferably about 70–100° C. and most preferably about 80–90° C. to form a hot solution. To the above solution, the required hot metal salt solution, at about 80–90° C., is added to the reaction mass to get the desired metal nicotinate. The resulting mass is then cooled to an ambient temperature, filtered, washed and dried to get the pure metal nicotinate.

In an another embodiment of the present invention chromium or zinc nicotinate is obtained by the reaction with of at least one metal salt selected from a group consisting of chromium (III) nitrate, chromium (III) chloride, chromium (III) acetate, chromium (III) formate, chromium (III) sulfate etc., for chromium nicotinate, zinc sulfate, zinc chloride, zinc acetate, zinc carbonate, etc., for zinc nicotinate An embodiment of the present invention provides a yield of about 77% zinc nicotinate.

An embodiment of the present invention provides a yield of about 75% chromium nicotinate.

The present invention is further described with the help of the following examples which are given by way of illustration and therefore should not be construed to limit the scope of the invention in any manner.

EXAMPLES

Example 1

1.0 kg beta picoline is slowly added to concentrated sulphuric acid under agitation. After complete addition, the reaction mass temperature is raised to 180° C., 7.6 kg of 56% nitric acid is added and the temperature is maintained at 180–190° C. for 20 hrs. After complete oxidation, the reaction mixture is cooled to an ambient temperature and diluted with 5.0 kg of water. After dilution, the pH of the reaction mixture is adjusted to pH 7.0 to 8.0 by the addition of an aqueous ammonia solution. The resulted solution is heated to 80–90° C. and a hot solution of 600 g of chromium (III) chloride in 2.5 kg water at 80–90° C. is added over a period of 2–6 hrs. The whole mass is maintained at 80–90° C. with stirring for further half an hour. The resulting mass is brought to an ambient temperature and the product is collected by filtration and washing. After drying, 980 g of purple colored chromium nicotinate, having a 12.7% chromium content, is obtained and 335 g of beta picoline is recovered from the filtrate.

Example-2

Example 1 was repeated by adopting the same procedure but chromium (III) acetate is used in place of the chromium (III) chloride.

Example-3

Example 1 is repeated by adopting the same procedure but chromium (III) oxalate is used in place of the chromium (III) chloride.

Example-4

Example 1 is repeated up to the oxidation step by adopting the same procedure and the reaction mass is diluted with 5.0 kg water. After dilution, the pH of the solution is adjusted to 7.0–8.0 by the addition of a liquid ammonia solution. The temperature of the resulted solution is raised to 80–90° C. and a hot solution (80–90° C.) of 975 g zinc sulphate heptahydrate in 2.0 kg water is added to the reaction mass slowly and the mass is concentrated and chilled to 0–5° C. The white precipitate that is formed is filtered, washed, reprecipitated with water and again filtered, washed and dried to give 500 g pure zinc nicotinate having a 21% zinc content. 330 g of unreacted beta picoline is recovered from the filtrates.

Example-5

Example 4 is repeated following the same procedure but zinc chloride is used in place of zinc sulphate.

What is claimed is:

1. A single pot process for the preparation of zinc and/or chromium nicotinates comprising the steps of:
   (a) hydrosulfonating beta picoline, by reaction with sulfuric acid at a temperature of about 35–100° C., to form a reaction mixture;
   (b) further heating the reaction mixture thus obtained to a temperature of about 150°–210° C.;
   (c) oxidizing the reaction mixture of step (b) with an oxidizing agent to form a solution containing nicotinic acid sulfate at a temperature of about 35–90° C.;
   (d) adjusting the pH of the solution of step (c) to a basic solution having a pH of about 7 to 8 and maintaining the pH of said solution;
   (e) treating the basic solution of step (d) with a water soluble zinc and/or chromium salt to produce a solid metal nicotinate in said water, and
   (f) filtering the resulting solid nicotinate to remove such from said water and to thereby obtain the corresponding metal nicotinates of high purity.

2. The process as claimed in claim 1, further comprising, in step (c), oxidizing said reaction mixture with a mixture of nitric acid and sulfuric acid.

3. The process as claimed in claim 1, wherein the reaction of beta picoline and sulfuric acid is carried out at about 35° to 90° C.

4. The process as claimed in claim 1, wherein the reaction of beta picoline with sulfuric acid is carried out at about 50 to 90° C.

5. The process as claimed in claim 1, further comprising heating the reaction mixture of step (c) to a temperature of about 150° to 210° C.

6. The process as claimed in claim 1, further comprising heating the reaction mixture of step (b) to a temperature of about 190° C. to 205° C.

7. The process as claimed in claim 1, further comprising removing nitric oxide fumes produced during oxidation through ventilation.

8. The process as claimed in claim 1, further comprising carrying out said oxidation for about 18 to 22 hours.

9. The process as claimed in claim 1, further comprising carrying out said oxidation for about 20 hours.

10. The process according to claim 1, further comprising cooling said reaction mixture of step e) to about an ambient temperature and then adjusting the pH of the reaction mixture to about 7.0 to 8.0.

11. The process as claimed in claim 1, further comprising adding water to the solution of step (c) before adjusting the pH of the solution.

12. A process of claim 1, wherein said alkali solution used comprises an aqueous ammonia solution.

13. A process as claimed in claim 1, wherein unreacted beta-picoline is recovered from the filtrate after the separation of metal nicotinates.

14. The process as claimed in claim 1, wherein said zinc salt used for the preparation of said zinc nicotinate is at least one member selected from the group consisting of zinc sulfate, zinc chloride, zinc acetate and zinc carbonate.

15. The process as claimed in claim 1, further comprising recovering zinc nicotinate having about 19 to 22% by weight zinc.

16. The process as claimed in claim 1, comprising recovering zinc nicotinate having about 21% by weight zinc.

17. The process as claimed in claim 1, wherein the metal salt used for the preparation of chromium nicotinates is at least one member selected from the group consisting of chromium nitrate, chromium chloride, chromium acetate, chromium formate, chromium carbonate and chromium sulfate.

18. The process as claimed in claim 1, comprising recovering chromium nicotinate having about 8 to 14% by weight of chromium.

19. The process as claimed in claim 1, comprising recovering chromium nicotinate having about 12.7 to 12.9% by weight of chromium.

20. The process as claimed in claim 1, further comprising washing and drying the filtered reaction product of step (f) under conditions sufficient to produce substantially pure metal nicotinate.

21. The process as claimed in claim 1, wherein the yield of zinc nicotinate is about 77%.

22. The process as claimed in claim 1, wherein the yield of chromium nicotinate is about 75%.

23. A single-pot process for the preparation of metal nicotinates comprising:
   hydrosulfonation of beta picoline with sulfuric acid to produce a reaction mixture;
   heating the reaction mixture thus obtained to an elevated temperature;
   oxidizing the heated reaction mixture under conditions sufficient to obtain nicotinic acid sulfate;
   reacting the nicotinic acid sulfate with a water soluble zinc and/or chromium salt to produce a solid metal nicotinate; and
   separating solid metal nicotinate of high purity from the reaction product.

* * * * *